United States Patent [19]
Buynak et al.

[11] 4,215,107
[45] Jul. 29, 1980

[54] PARAINFLUENZA VIRUS VACCINE AND ITS PREPARATION

[75] Inventors: Eugene B. Buynak, North Wales; Maurice R. Hilleman, Lafayette Hill, both of Pa.

[73] Assignee: Merck & Co., Inc., Rahway, N.J.

[21] Appl. No.: 974,396

[22] Filed: Dec. 29, 1978

Related U.S. Application Data

[63] Continuation-in-part of Ser. No. 817,955, Jul. 22, 1977, abandoned.

[51] Int. Cl.$^2$ ............................................. A61K 39/12
[52] U.S. Cl. ...................................... 424/89; 435/237
[58] Field of Search ............................. 424/89; 195/1.3

[56] References Cited

FOREIGN PATENT DOCUMENTS 2323847  11/1974  Fed. Rep. of Germany .

OTHER PUBLICATIONS

Potash et al., J. Infect. Dis. 121 (6):640–647, Jun. 1970, A Mutant of Parainfluenza Type I Virus with Decreased Capacity for Growth at 38° C. and 39° C.
Schieble et al., Chem. Abstr. 80, #66916m (1974), Potential Respiratory Vaccine Strains and Isolation Methods, U.S. Nat. Tech. Inform. Serv. PB Rep. 1973, No. 221701/6, 11 pp.
Tint et al., Chem. Abstr., 78, #128374 (1973), To Provide a Base for Others Against Viral Agents in Respiratory Illness, U.S. Nat. Tech. Inform. Serv. PB Rep. 1972, No. 213497/1, 33 pp.
Straub Chem. Abstr. 82, #90062s (1975) of Ger. Offen. 2,323,847 Living Parainfluenza 3 Vaccine.
Shitikiva et al., Biol. Abstr. 65 (9), 53586, May 1, 1978 of Vopr. Virusol. (4):445–449, 1977, Recd. 1978, The Interfering and Interferon-Inducing Activity of Attenuated and Original Parainfluenza Virus Strains.

*Primary Examiner*—Shep K. Rose
*Attorney, Agent, or Firm*—Donald J. Perrella; Julian S. Levitt

[57] ABSTRACT

By serially passaging virulent parainfluenza virus in tissue culture prepared from embryonated hens' eggs or human diploid lung fibroblasts, a live, non-pathogenic but antigenic live parainfluenza virus is produced. This virus is useful in preparing a live virus vaccine.

13 Claims, No Drawings

4,215,107

PARAINFLUENZA VIRUS VACCINE AND ITS PREPARATION

RELATED APPLICATION

This application is a continuation-in-part of our copending application Ser. No. 817,955 filed July 22, 1977.

BACKGROUND OF THE INVENTION

1. Field of the Invention

This invention relates to a vaccine for parainfluenza virus and to a method for producing the vaccine. More particularly, it relates to an attenuated, live parainfluenza virus for human administration to protect against infection, and to the method for preparing the attenuated virus strain.

Parainfluenza viruses, members of the myxovirus family, were discovered in 1952. These viruses are a major cause of respiratory infections, especially in children, where life-threatening upper and lower respiratory tract infections occur. The clinical spectrum includes pharyngitis, bronchitis, croup, and bronchopneumonia. It has been reported that parainfluenza virus types 1, 2 and 3 are associated with approximately a third of the cases of acute laryngotracheobronchitis and 8 to 17 percent of the cases of bronchopneumonia in infants and children. In adults, these viral agents occasionally cause upper respiratory tract infection and uncommonly, pneumonia.

2. Objects of the Invention

It is, accordingly, an object of the present invention to provide a safe, effective parainfluenza virus. Another object is to provide a parainfluenza virus which is antigenic while nonpathogenic. A further object is to provide a parainfluenza vaccine which protects against the effects of this virus on both initial and subsequent challenge. Still another object is to provide physiologically acceptable compositions for administering parainfluenza vaccine. Yet another object is to provide a method for attenuating parainfluenza virus. Another object is to provide a method for preparing a parainfluenza virus vaccine. These and other objects of the present invention will be apparent from the following description.

SUMMARY OF THE INVENTION

It has now been found that a live, attenuated nonpathogenic but antigenic live parainfluenza vaccine is produced by serially passaging isolated, adapted virulent parainfluenza virus in tissue culture from embryonated hens' eggs or human diploid lung fibroblasts.

DETAILED DESCRIPTION

In general terms, the invention is concerned with the adaptation and propagation of parainfluenza types 1, 2 and 3 in tissue cultures prepared from embryonated hens' eggs, or human diploid lung fibroblasts. More particularly, this invention is directed to the development of live virus vaccines against the parainfluenza group of agents following serial passage in chick embryo tissue culture, or human diploid lung fibroblasts. This procedure involves the steps of (A) the isolation of the virulent viruses in any of a variety of cells in culture, and its adaptation to chick embryo tissue culture or human diploid lung fibroblasts; (B) the development of the attenuated viruses by a plurality of serial passages in chick embryo tissue culture or human diploid lung fibroblasts; and (C) the preparation of the vaccines from these attenuated live viruses. These steps will be separately explained.

A. Isolation and Adaption of Virulent Virus

Isolation and adaptation of parainfluenza virus types 1 and 3 can be accomplished by at least 1 and preferably at least from 3 to 5 passages in monkey kidney cell culture. Isolation and adaptation of parainfluenza virus type 2 can be accomplished by at least 1 and preferably at least from 3 to 5 passages in monkey kidney cell culture followed by at least 1 preferably from 3 to 5 passages in embryonated hens' eggs, preferably via the amniotic route. Isolation in the above mentioned cell cultures can be from clinical material (e.g., throat swab). Incubation of infected cultures can be carried out at any temperature between about 30° and about 38° C., preferably at 30°–34° C. (optimal 32° C.) or at 35° to 38° C. (optimal 36° C.).

B. Development of Attenuated Live Parainfluenza Virus Vaccine

The virus which has been established by the foregoing isolation and adaption procedure to be parainfluenza virus is added to glass bottles containing chick embryo tissue cultures prepared from minced and trypsinized approximately ten-day-old chick embryos for types 2 or 3, or for type 1 human diploid lung fibroblasts such as WI-38 fibroblasts as described in Exper. Cell Res., 25, 585 (1961). A cell line of WI-38 fibroblasts has been deposited with the American Type Culture Collection and given accession number CCL-75. The culture medium may be any of those which support cell growth and this may be, for example, the known medium 199 to which calf serum has been added or Eagle's minimal essential medium (MEM) in Eagle's balanced salt solution (BSS) supplemented with prescreened calf serum. After the addition of the virus, the infected cell cultures are incubated in successive passages at 30°–38° C. and preferably at 30°–34° C. (optimal 32° C.) and 35°–38° C. (optimal 36° C.). During these passages the virus is replicated in large amount and becomes attenuated.

The above serial passages are performed using undiluted or diluted inoculum and multiple harvests are collected at various intervals. Infectivity titrations are performed in grivet monkey kidney tissue cultures.

C. Preparation of Vaccine From Attenuated Virus

The parainfluenza virus harvested after this repeated serial passage is found to be nonpathogenic for monkeys and rodents, to cause little or no clinical reactions in human recipients, and to evoke a satisfactory level of neutralizing antibody. The virus infectivity is stabilized by a suitable stabilizer such as sucrose, phosphate, glutamine, human albumin, or mixtures thereof. After titration to establish its potency, the virus pool is subdivided and filled into appropriate vials for use. The product can be stored frozen or preferably dried from the frozen state and kept free of moisture.

The following examples illustrate the present invention without, however, limiting the same thereto.

EXAMPLE 1

The inoculum is parainfluenza virus type 1 which is obtained as described in A above after 3 passages in grivet monkey kidney (GMK) cell culture, and 10 passages in human diploid lung fibroblasts (WI-38). The WI-38 human diploid lung fibroblasts are prepared in glass bottles using BME supplemented with 10% unheated fetal calf serum as growth medium. Two days post-planting, the growth medium is decanted, and the cultures inoculated with 5.0 ml of undiluted or diluted seed per bottle. Following an adsorption period of one hour at 30°-34° C., 100 milliliters of MEM containing 2 percent unheated fetal calf serum are added to each bottle, and re-incubated at 30°-34° C. Three to four days post-seeding, the bottle cultures are washed four times with Hank's PBS, 100 mililiters per wash. Following the washing procedure, 100 milliliters of MEM containing a suitable viral stabilizer, e.g., sucrose, phosphate, glutamate, is added to each bottle and the cultures incubated at 30°-34° C.

Neomycin at a concentration of 50 mcg/ml is incorporated in the growth and maintenance medium. Multiple harvests are collected at 2-4 day intervals and the bottle cultures are refed with fresh maintenance medium containing stabilizer. A viral stabilizer, e.g., sucrose, phosphate, glutamate, is added in appropriate amounts prior to shell freezing and storage at −70° C. (electrically operated). One or more appropriate harvests are selected following completion of infectivity titrations. The selected material is removed from the freezer and thawed. A sample is removed for control and safety testing. The remaining fluid is clarified and a sample removed for monkey safety testing. The fluids are distributed into individual vials and lyophilized. Following the lyophilization cycle, the vials are capped, sealed, and retained for reconstitution as a vaccine by the addition of sterile water (Water for Injection, U.S.P.).

The potency of the product is based on infectivity titration in GMK cell culture.

EXAMPLE 2

The procedure of Example 1 is carried out but the incubation of the parainfluenza virus type 1 is in the 35°-38° C. range and close to 36° C.

EXAMPLE 3

The inoculum is parainfluenza virus type 2 which is obtained as described in A above after 2 passages in grivet monkey kidney cell culture, 8 passages in embryonated hens' eggs, and 10 passages in chick embryo tissue culture. Nine to eleven-day-old chick embryos, after removal of the head and extremities, are finely minced under aseptic conditions and the minced tissued washed in several changes of Hank's Balanced Salt Solution (BSS). The washed tissue is trypsinized at 36° C. using 0.25% trypsin (Difco 1:250) in tris saline buffer for approximately two hours. The trypsin-cell suspension is harvested through two thicknesses of sterile cheese cloth and centrifuged at 1500 rpm for five minutes. Packed cells are resuspended in growth medium for counting. Growth medium consists of medium 199 (Morgan, J. F., Morton, H. J., and Parker, R. C., Proc. Soc. Exp. Biol. and Med., 73: 1-8, 1950) containing 2% unheated fetal calf serum and 50 mcg/ml neomycin. Bottle cultures are planted at a concentration of 700,000 viable cells per milliliter. Following incubation at 36° C. for 48 to 72 hours, bottle cultures can be used for serial passage or vaccine preparation.

Chick embryo tissue cultures are prepared in glass bottles using medium 199 containing 2% unheated fetal calf serum as growth medium. Three to four days post-planting, the growth medium is decanted and the cultures inoculated with 5.0-10.0 ml of undiluted or diluted seed virus per bottle. Following an adsorption period of one hour at 30°-34° C., 70 milliliters of medium 199 containing 2% agamma calf serum is added to each bottle, and re-incubated at 30°-34° C. Three to four days post-seeding, the bottle cultures are washed four times with Hanks' BSS, 100 milliliters per wash. Following the washing procedure, 100 milliliters of medium 199 containing a suitable viral stabilizer is added to each bottle and the cultures in cubated at 30°-34° C. Neomycin at a concentration of 50 mcg/ml is incorporated in the growth and maintenance medium. Multiple harvests are collected at 2-4 day intervals and the bottle cultures are refed with fresh maintenance medium containing stabilizer. Infectivity titrations of each harvest are performed in grivet monkey kidney tissue cultures. Each harvest is collected aseptically into a sterile container, samples removed for microbial sterility testing and the remainder is shell-frozen in a dry ice-alcohol bath. The virus-containing fluids are stored at 70° C. in an electrically operated freezing unit prior to selection of a harvest or harvests for preparation of the vaccine.

Appropriate harvest or harvests are selected following completion of infectivity titrations. The selected material is removed from the freezer and thawed. A sample is removed for control and safety testing. The remaining fluid is clarified and a sample removed for monkey safety testing. Appropriate additional stabilizer, as mentioned above, is added to the remaining fluid. The fluids are distributed into individual vials and lyophilized. Following the lyophilization cycle the vials are capped, sealed and retained for reconstitution as a vaccine by the addition of sterile water (Water for Injection, U.S.P.).

The potency of the product is based on infectivity titrations in grivet monkey kidney cell cultures.

Tests in man.

Clinical studies of parenterally administered parainfluenza virus type 2 (monovalent vaccine) was conducted in children. Good antibody responses were observed with little, if any, untoward clinical reactions.

EXAMPLE 4

The procedure of Example 2 is repeated except employing parainfluenza virus type 2.

EXAMPLE 5

The procedure of Example 1 is repeated except substituting parainfluenza virus type 3 and eliminating the passages in embryonated hens' eggs. The inoculum is parainfluenza virus type 3 which is obtained as described in A. above by employing 1 passage in grivet monkey kidney tissue and 9 passages in chick embryo tissue culture. Similar clinical results are obtained.

EXAMPLE 6

The procedure of Example 2 is repeated except employing parainfluenza virus type 3.

What is claimed is:

1. A process of preparing a live, attenuated parainfluenza virus types 1 or 3 comprising isolating and adapting the virus by at least 1 passage in monkey kidney cell culture and serially passaging the virus at least 3 times in human diploid lung fibroblasts for type 1 or at least 3 times in chick embryo cell culture for type 3.

2. A process of preparing a live, attenuated parainfluenza virus type 2 comprising isolating and adapting the virus according to claim 1, serially passaging the virus at least once in embryonated hens' eggs, and serially passaging the virus at least 3 times in chick embryo cell culture.

3. A process according to claim 1 wherein the type 1 parainfluenza virus is isolated and adapted by at least three passages in monkey kidney cell culture.

4. A process according to claim 1 wherein the type 3 parainfluenza virus is isolated and adapted by at least three passages in monkey kidney cell culture.

5. A process according to claim 2 wherein the parainfluenza virus type 2 is isolated and adapted by at least three passages in monkey kidney cell culture, and at least 3 passages in embryonated hens' eggs.

6. A process according to claim 2 wherein the serial passage in embryonated hens' eggs is carried out via the amniotic route.

7. A process according to claim 1 wherein the isolation and adaption is carried out at from about 30° to about 38° C.

8. A process according to claim 2 wherein the isolation and adaption is carried out at from about 30° to about 38° C.

9. A parainfluenza vaccine comprising a live attenuated antigenic and immunogenic parainfluenza virus type 1, type 2 or type 3 adapted for human administration by at least one passage in monkey kidney cell culture and for type 1, at least 3 serial passages in human diploid lung fibroblasts, and for type 2 at least one passage in embryonated hens' eggs and at least 3 serial passages in chick embryo cell culture, and for type 3 at least 3 serial passages in chick embryo cell culture.

10. A composition comprising the attenuated suitable of claim 9 together with a viral stabilizer.

11. A liquid composition according to claim 10 in frozen state.

12. A composition according to claim 10 in lyophilized state.

13. A composition according to claim 10 wherein the stabilizer comprises sucrose, phosphate, glutamine, human albumin or mixtures thereof.

* * * * *

UNITED STATES PATENT AND TRADEMARK OFFICE
CERTIFICATE OF CORRECTION

PATENT NO. : 4,215,107
DATED : July 29, 1980
INVENTOR(S) : Eugene B. Buynak and Maurice R. Hilleman It is certified that error appears in the above-identified patent and that said Letters Patent are hereby corrected as shown below:

Claim 10. should read as follow:

Claim 10. A composition comprising the attenuated virus of Claim 9 together with a suitable stabilizer.

Signed and Sealed this

Second Day of June 1981

[SEAL]

Attest:

RENE D. TEGTMEYER

Attesting Officer

Acting Commissioner of Patents and Trademarks